US009575017B2

(12) United States Patent
Jiang et al.

(10) Patent No.: US 9,575,017 B2
(45) Date of Patent: Feb. 21, 2017

(54) HIGH PERFORMANCE KRATKY ASSEMBLY

(71) Applicant: Rigaku Innovative Technologies, Inc., Auburn Hills, MI (US)

(72) Inventors: Licai Jiang, Rochester Hills, MI (US); Paul Ulrich Pennartz, Eschweiler (DE)

(73) Assignee: Rigaku Innovative Technologies, Inc., Auburn Hills, MI (US)

( * ) Notice: Subject to any disclaimer, the term of this patent is extended or adjusted under 35 U.S.C. 154(b) by 73 days.

(21) Appl. No.: 14/187,832

(22) Filed: Feb. 24, 2014

(65) Prior Publication Data

US 2015/0241366 A1 Aug. 27, 2015

(51) Int. Cl.
*G21K 1/02* (2006.01)
*G01N 23/201* (2006.01)
*G21K 1/04* (2006.01)

(52) U.S. Cl.
CPC ............ *G01N 23/201* (2013.01); *G21K 1/02* (2013.01); *G21K 1/025* (2013.01); *G21K 1/04* (2013.01); *G21K 2201/062* (2013.01)

(58) Field of Classification Search
CPC ... G01N 23/201; C08K 5/5406; C09D 127/12; B82Y 10/00; B82Y 30/00; C08L 2666/14; C08L 27/12; C08L 83/00; G21K 1/06; G21K 2201/061; H01L 51/0035; H01L 51/0077; H01L 51/0084
See application file for complete search history.

(56) References Cited

U.S. PATENT DOCUMENTS

| 4,028,547 | A * | 6/1977 | Eisenberger | G03F 7/702 378/85 |
| 7,139,366 | B1 * | 11/2006 | Jiang | 378/88 |
| 2006/0269045 | A1 * | 11/2006 | Jiang | G01N 23/20008 378/86 |
| 2007/0003013 | A1 * | 1/2007 | Matsuo et al. | 378/84 |
| 2007/0007464 | A1 * | 1/2007 | Lange | G01N 23/201 378/86 |
| 2013/0315375 | A1 * | 11/2013 | Kleine | G01N 23/20008 378/71 |

FOREIGN PATENT DOCUMENTS

DE 10 02 138 B 2/1957

OTHER PUBLICATIONS

Bergmann et al., " Improvement of SAXS measurements on Kratky slit systems by Gobel mirrors and imaging-plate detectors", Journal of Applied Crystallography, (2000), 33, pp. 869-875.*

* cited by examiner

*Primary Examiner* — Glen Kao
(74) *Attorney, Agent, or Firm* — Brinks Gilson & Lione

(57) ABSTRACT

An assembly for Kratky collimator is provided. The assembly may be used for a small angle x-ray camera or system requiring such filtering. The assembly may include a first block with a first working surface and a second block with a second working surface. The first and second blocks may be aligned with the first working surface pointing an opposite direction of the second working surface and the first working surface being aligned in a common plane with the second working surface. In some implementations, the first block may comprise a crystal material. In some implementations, an extension may of the first block may be configured position a beamstop.

20 Claims, 2 Drawing Sheets

HIGH PERFORMANCE KRATKY ASSEMBLY

BACKGROUND

1. Field of the Invention

The invention relates to a Small Angle X-ray Scattering (SAXS) measurement system which uses Kratky assembly for beam conditioning.

2. Description of the Known Art

Kratky collimation has been used to create a parasitic scattering-free data collection space. Kratky collimation assemblies have been used by the traditional 1D Kratky camera and some newer 2D SAXS system (U.S. Pat. No. 7,734,011). The quality of the Kratky collimation assembly may be important to the performance of a small angle x-ray scattering (SAXS) camera to eliminate parasitic scattering. Specifically, the flatness of the working surfaces, alignment between the surfaces of the two blocks and the scattering characteristics of the Kratky blocks affect the background "cleanness" and the total flux on the sample for a given system resolution (Qmin). These qualities are elements that determine the highest resolution, the lowest Qmin, and the performance consistency the system can achieve. Mechanical stability of the system over time determines the system performance consistency over time.

SUMMARY

In order to align the surfaces of the two blocks within the same plane, one of the blocks may be made in "U" shape, e.g. a block with two arms extended from the block. The surfaces of the "arms" and the surface of the block may be grinded, lapped and polished simultaneously so that the surface of the "arms" and the surface of the block are exactly in the same plane. Then the other block is attached to the "arms" of the first block with its well finished surface facing the arms without any gap. In this way, the working surfaces of the two blocks are guaranteed to be within the same plane.

To address the long term stability of the Kratky blocks, the materials, typically steel and steel alloy, are annealed and well-aged.

Still the problems may exist when used in certain applications. First of all, material annealing and aging are tedious and may not easily guarantee the high degree of stability required by the ultra-low Qmin applications. Secondly, X-rays interact with the Kratky blocks at the corners of each block and produce parasitic scattering. Mathematically such scattering would be totally blocked by the surface of the block near to the sample from entering the data collection zone. However, any contamination on the surface of the block, which is out of the defined plane by the two blocks, would further scatter the parasitic scattering into the data collection zone, thus increase the Qmin.

The disclosed systems and methods provided improve performance of the Kratky blocks by addressing the two issues discussed above. Single crystal is a stress free material. Using a single crystal material will essentially eliminate the stress related stability problem. Interaction between x-rays and the single crystal material also yield much less parasitic scattering. Both in theory and practical experiments, it has been proved that the parasitic scattering can be reduced by three orders of magnitude by using single crystal material. Therefore, with the same degree of contamination to the Kratky blocks, the parasitic scattering from a single crystal block can be three orders of magnitude less than that from a steel alloy block, and the single crystal block will require much less maintenance and result in much less system down time.

Another minor issue in some camera designs is the alignment issues related to the resolution change. Carefully aligning the angle between the primary beam and the Kratky blocks will give different trade-offs between the flux passing through the system and the system resolution. It is highly desired to be able to change the system for different resolution requirements. However, for each change of the system resolution, one has to realign the beamstop which blocks the primary beam from entering the detector. It is desirable to design the beamstop as part of the Kratky blocks so that aligning the Kratky block would automatically reposition the beamstop.

An improved Kratky assembly is provided in this disclosure. The Kratky assembly includes a first block and a second block. The first block may be formed from a crystal material. The second block may be formed of either crystal material or other heavy element material, and the two blocks may be aligned with the working surface of each block being aligned within a common plane.

DETAILED DESCRIPTION

Figure 1:
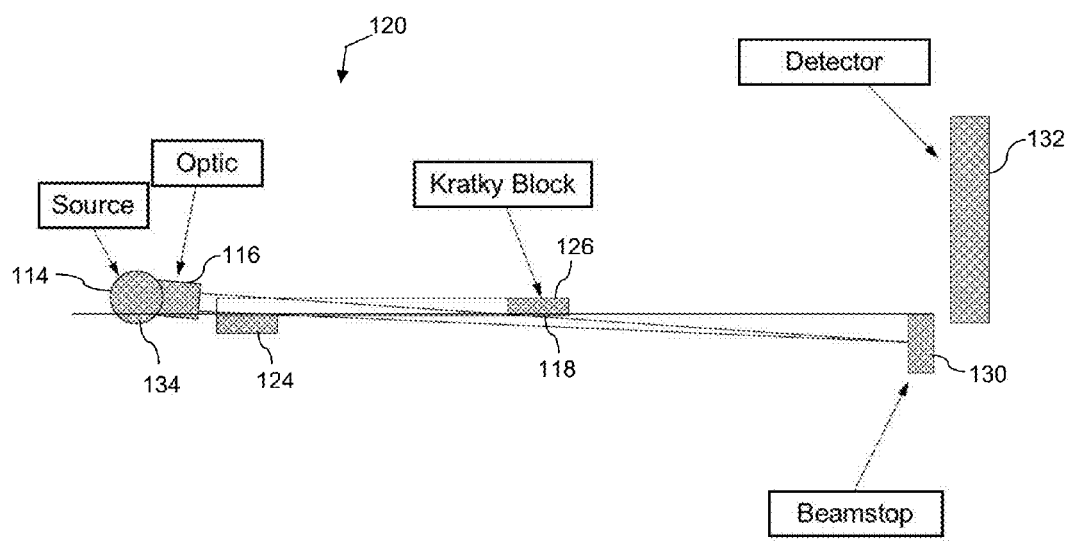
FIG. 1 is side view of a SAXS camera including a Kratky assembly.

A system for improving a Kratky collimation assembly to provide a parasitic scattering free data collection zone is provided. The Kratky collimation assembly may be integrated within a SAXS Instrument. The Kratky collimation assembly may be made of single crystal or mosaic crystal. The single crystal or mosaic crystal may be stress free or with minimized stress. Using a single crystal or mosaic crystal simplifies the manufacturing process, reduces the need of annealing and provides long term stability. The single crystal material also produces much less parasitic scattering and is much less prone to the contamination which may further scatter the parasitic scattering into the data collection zone, thus reduces the need of maintenance. Further, a beamstop may be pre-fixed with the Kratky collimation assembly. In one exemplary implementation, the adjustment of the Kratky blocks will carry the beamstop so that the beamstop remains aligned with the Kratky blocks. The fixed relationship between the beamstop and the Kratky blocks may simplify the adjustment procedure and provide consistent system performance.

A Kratky assembly may be formed using two blocks. The first block of the two blocks may have an extended bridge to the position where the second block should be attached. The part of the bridge of the first block at the position where the second block is attached may share the same plane as the working plane of the first block. For example, the surface of the bridge extending from the first block to where the second block is attached, may be a natural extension of the working surface of the first block and may be in the same plane as the working surface of the first block.

The block close to the sample generally has a predefined width. The width of the surface is used to block the parasitic scattering. The width of the block, typically 20 mm or wider, depends on the precision of the surface finishing. The width of the block close to the source does not have to be wide. In fact, a thin blade would be sufficient as long as the block can block the x-rays.

The working surfaces are ground, lapped and polished with very high precision and very low micro-roughness. Kratky collimation assembly may be made of hardened steel or other metal material. These materials typically have internal stress. In order to minimize the future deformation of the collimation assembly, the materials may be annealed and aged before being used. The annealing process may include annealing with elevated temperature and long shelve time for natural annealing.

The metal annealing and polishing can be lengthy and complicated processes. These processes can be especially challenging for long Kratky collimation assemblies. Simplified processes and material choices warranting better time stability may provide significant improvements in performance and cost especially for long Kratky assemblies.

In some implementations, crystal materials may be used to form the working surfaces of the Kratky blocks. Crystal materials, such as Si single crystal and Ge single crystal, are widely available materials which are essentially free of stress. Single crystal materials can be easily machined, ground, lapped and polished to very high precisions. As a material for fabricating a Kratky assembly, one weakness of single crystal materials is low stopping power. However, for the block closer to the sample, the penetration is not an issue for blocking parasitic scattering to the data collection zone. For the block closer to the source, on the other hand, the penetration of x-rays could produce some scattered x-rays beyond the plane defined by the working surfaces of the Kratky blocks into the data collection zone. These x-rays scattered by the penetration through the first block may contaminate the data collection zone. Therefore, the block near to the source may need a higher stopping power. As such, the block near to the source may be formed from a heavier element than the block closer to the sample, such as germanium or metal.

Single crystal materials may also produce much lower parasitic scattering due to their lack of defects. An assembly with low parasitic scattering from the interaction between Kratky blocks and x-rays will have an increased tolerance to surface imperfection and surface contamination. Therefore, a Kratky assembly made of single crystals may provide better performance and require less maintenance.

Now referring to FIG. 1, a side view of a small angle x-ray scattering system is provided. The small angle x-ray system includes an x-ray source 114, an optic 116, Kratky assembly 120, and a detector 132. The x-ray source 114 may be a line source or a point source. The x-ray source may be a micro-focusing source, rotating anode, or other known source. The source 114 may emit an x-ray beam 118 that is received by an optic 116. The optic 116 may be a one-dimensional optic or two-dimensional optic. A two-dimensional optic conditions the beam in two orthogonal dimensions perpendicular to the beam propagation. The optic 116 may be a crystal optic or a multi-layer optic. Further, the optic 116 may be a side-by-side KB optic or sequential KB optic. The optic 116 conditions the x-ray beam and directs the x-ray beam toward the Kratky assembly 120. The Kratky assembly includes a first block 126 and a second block 124. The x-ray beam interacts with the second block of the pair of Kratky blocks 124, 126. The working surface of the second block 124 (second working surface) interacts with x-rays to define one side of the x-ray beam.

The beam is also defined by the edge of the working surface of the first block 126 (first working surface). The working surface of the first block 126 may be located substantially in plane with the working surface of the second block 124. Therefore the working surface of the block 124 and the working surface of the block 126 create a parasitic scattering free zone beyond the plane which may be called the "Kratky plane". Line 134 is a projection of the primary beam on to the Kratky plane. The angle between line 134 and the primary beam is $2\theta_{min}$. It is understood that the second block 124 may be an edge or other device such that the tip of the edge extends substantially in plane with the working surface of the first block 126.

The basic function of the Kratky assembly 120 in a SAXS instrument is to form a beam with a clean background near the primary beam for collecting weakly scattered x-rays from a sample. The Kratky assembly 120 uses the blocks to cut the background of the beam, but meanwhile its interaction with incident x-rays may generate parasitic scattering. Kratky assembly uses the common plane of the blocks (plane 134) to block the parasitic scattering x-rays from reaching the space above the plane 134, thus create a data collection space, in theory, without any background. On the other hand, the flatness and the micro-roughness of the blocks' surfaces, and the alignment of the two surfaces, impact the performance. In other words, how low a background one can get depends on the quality of the Kratky blocks in terms of the flatness and the microroughness of the working surfaces, as well as the alignment between the two surfaces. In addition, the surface contamination may act as scattering sources to scatter the parasitic scattering into the data collection zone.

The first block 126 may be made of a crystal material such as single crystal or mosaic crystal. The crystal materials include Si crystal and/or Ge crystal. The stress free characteristics of crystal materials may improve the stability of the first block 126. The first block may be made with a single arm or two arms extended towards the second block. The surfaces of the extended arms are the extension of the working surface of the first block. The second block 124 may be attached to the arms of the first block 126. Accordingly, the working surface of the second block 124 may be precisely aligned with the working surface of the first block 126. The first block 126 may be made of the same crystal material as the second block 124. In some implementations the second block 124 may be made of a material with higher absorption power than the first block 126, such as Ge crystal or a metal material.

The beamstop 130 may extend to the kratky plane at 134 (the parasitic scattering free plane). The sample 128 may cause scattering of the beam which may be received by detector 132. A portion of the beam will continue through the sample and be received by the beamstop 130. The beamstop is used to block the portion of the beam that is directly transmitted through the sample without being scattered into the parasitic scattering free zone, so the detector 132 will not be over saturated and the detection of the scattering from the sample 128 will not be interfered.

The quality of a Kratky collimation assembly may be measured by the scattering at the corners where x-rays interact with the blocks. Although the scattering does not affect the data collection zone for a well aligned and well-polished Kratky assembly, a high level scattering from corners of the blocks widens the primary beam slightly. In addition, the strong parasitic scattering might get into the data collection zone by secondary scattering caused by the imperfection of the working surface of the first block or contaminants of the first block. It imposes a higher degree of polishing on the working surfaces of the Kratky blocks and strict maintenance of the surfaces cleanliness.

As described above, in order to precisely align the two Kratky blocks, one block may be designed to include a bridge. The bridge may share the same plane with the working planes of the two Kratky blocks. The bridge may extend from the first block to the position when the second block should be. The second block may be attached to the bridge. For example, the working plane of the second block may be directly (gapless) attached to the plane of the bridge. The first block may be designed with a "U" shaped structure and the second block may be attached to the "arms" of the "U" shaped structure. As such, the working surface of the first block may be naturally aligned to the working surface of the second block. In this example, the accuracy of the alignment is the surface accuracy of the blocks and bridge.

Figure 2:
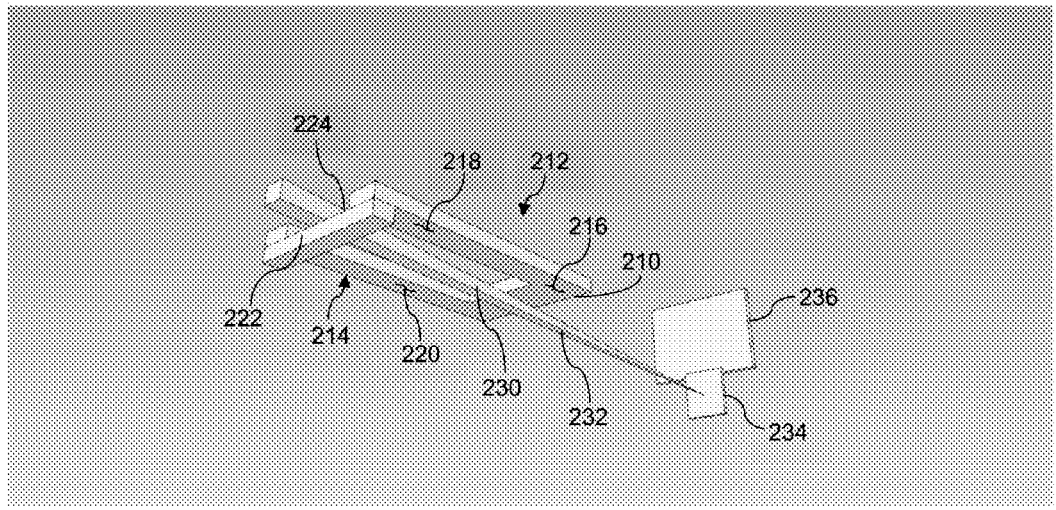
FIG. 2 is perspective view of a Kratky assembly including a bridge between a first block and a second block.

Now referring to FIG. 2, a perspective view of Kratky assembly with a bridge is provided. To achieve a precision alignment between the two working surfaces, one of the blocks, for instance the first block 210, may be made with bridge arms 212, 214. The working surface 216 of the first block 210 and the surfaces 218, 220 of the bridge arms 212, 214 are machined in the same common plane. In addition, the second block 222 is attached to the arms 212, 214. For example, the working surface 224 of the second block 222 may be facing the surfaces 218, 220 of the arms 212, 214 (and thus the working surface 216 of the first block 210). The block with the bridge arms may be made as a "U" shape. The "U" shape maybe a unitary piece made of a single crystal material.

Also referring to FIG. 2, where the "U" shaped first block is shown. In practice, the first block could also be a block with a "U" shaped front surface, e.g. it may be made of a block with a recess which forms a "U" shaped flat and polished surface and the recess of the block forms a passage for the x-ray beam.

Single crystal material, such as single crystal Si and single crystal Ge, may be used for the first block 210 and/or the second block 222. The working surface 216 of the first block 210 and/or the working surface 224 of the second block 222 may be formed from the single crystal material. Further, the bridge arms 214 and 212 may be formed of the single crystal material. Single crystal materials are normally considered stress free. Single crystal materials are also known to be easily machined to have a very flat surface and very low micro-roughness. Compared to metal, single crystal materials, such as Si and Ge, have relatively higher transparency and, therefore, lower stopping power to x-rays. However, using single crystal for the first block 210 near to the sample is generally acceptable. The slightly higher transparency does not cause any parasitic scattering in the data collection zone.

On the other hand, the higher transparency of the second block 222 far from the sample may result in points where x-rays interact with the block material off the block common plane due to the penetration of the x-rays. As such, the penetration creates a risk that parasitic x-rays may be generated that can reach the data collection zone. The seriousness of this issue depends on the density of the material and the x-ray energy. Using a high Z material can eliminate the problem. The second block 222 may be attached to the first block 210, but it may be relatively small and far from sample. Using a stress free material and having perfect surface finish is less important for the second block 222 than for the first block 210 (the block near to the sample), which requires an extended flat surface to block the parasitic scattering x-rays from entering the data collection zone.

As described above, using single crystal materials for the Kratky blocks has another advantage. Some of the parasitic scattering generated due to the interaction between the x-rays and the blocks propagate among the surfaces of the Kratky blocks, especially the block surface near to the sample. Surface imperfection or surface contamination would cause secondary scattering which will have higher chance to reach the data collection region. This is particularly a problem if the interest region is very close to the primary beam, e.g. the so called low Q region. Single crystal materials have much lower parasitic scattering when interacting with x-rays. Therefore, using Kratky blocks made of single crystal materials will provide easier finishing and maintenance of the working surfaces.

Another aspect of alignment in a SAXS camera is related to the alignment of the beamstop. Kratky collimation provides an easy method to adjust the tradeoff in a SAXS camera between the amount of flux provided to the sample and the resolution of the system. Rotating the Kratky assembly to provide a larger opening with respect to the beam will increase the flux on sample. Alternatively, rotating the Kratky assembly to provide a smaller opening with respect to the beam and a smaller angle between the beam and the Kratky plane will increase the resolution of the system. However, the beamstop which blocks the direct beam should also be adjusted accordingly. The precision of the beamstop adjustment directly affects the system performance. The alignment precision of the beamstop relative to the Kratky assembly becomes even more critical as the system resolution increases. The required accuracy of the beamstop alignment often needs to be less than a few tens of microns.

Figure 3:
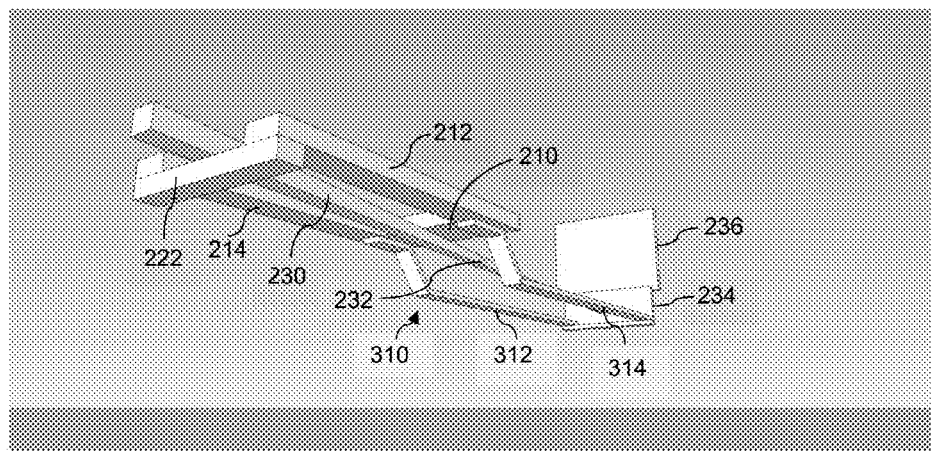
FIG. 3 is perspective view a Kratky assembly including a bridge between collimating blocks and a beamstop.

To make the change of system resolution easy and fast, the beamstop 234 can be attached to the Kratky assembly through an extension 310, for example formed of arms 312, 314, as shown in FIG. 3. The extension can be in the form of mounted arms, or an "H" shaped block where the arms of the beamstop can be made from one piece of material with the first block 210. In one example, the first block 210, the arms 212, 214 of the bridge extending to the second block 222, and the arms 312, 314 extending from the first block 210 to the beamstop 234 may be formed of a single piece of material and form an "H" shaped block. For example, the arms or the entire "H" shaped block may be formed from any of the single crystal materials described above. As such, rotation of the blocks 210, 222 mechanically cause rotation of the extension and adjustment in the position of the beamstop 234. In this case, one can adjust the system resolution without additional adjustment of the beamstop.

While this disclosure has been particularly shown and described with references to a preferred embodiment thereof, it will be understood by those skilled in the art that various changes in forms and details may be made therein without departing from the spirit and scope of this disclosure. Those skilled in the art will recognize or be able to ascertain using no more than routine experimentation, many equivalents to the specific embodiments described specifically herein.

The invention claimed is:

1. A Kratky assembly comprising:
   a first block made of crystal material with a first working surface, the working surface being flat and polished;
   a second block made of either crystal material or heavy element material with a second working surface, the first and second blocks being aligned with the first working surface pointing an opposite direction of the second working surface and the first working surface being aligned in a common plane with the second working surface.

2. The assembly of claim 1, wherein the second working surface is flat and polished.

3. The assembly of claim 1, wherein the first block has an extended bridge, and the second block being attached to the bridge with the second working surface being against a working surface of the bridge.

4. The assembly of claim 3, further comprising a beamstop and a bridge attached to the assembly being configured to position the beamstop.

5. The assembly of claim 3, wherein the first block and the extended bridge form a "U" shaped block with two arms extending from the first block, the "U" shaped block having a flat and polished surface extending from the working surface of the first block to the working surfaces of the two arms, where the second block is attached with the second working surface against the working surface of the bridge arms.

6. The assembly of claim 3, wherein the said second block is a blade attached to the bridge of the first block and the second working surface is an edge of the blade.

7. The assembly of claim 1, wherein the crystal material comprises a single crystal material.

8. The assembly of claim 7, the single crystal material is single crystal silicon.

9. The assembly of claim 7, the said single crystal material is single crystal germanium.

10. The assembly of claim 1, wherein the crystal material is mosaic crystal material.

11. A small angle x-ray system comprising:
an x-ray source configured to generate a beam;
an optic configured to direct the beam toward a sample;
a detector configured to receive scattering of the beam from the sample;
a first block made of crystal material with a first working surface, the working surface being flat and polished;
a second block with a second working surface, the first and second blocks being aligned with the first working surface pointing an opposite direction of the second working surface and the first working surface being aligned in a common plane with the second working surface, the first block and the second block being positioned between the optic and the sample and being configured to form a parasitic scattering free zone after the sample and behind a plane defined by the either the first or second working surface nearest to the sample such that detector is able to collect data free from parasitic scattering in the parasitic scattering free zone.

12. The system of claim 11, wherein the first block has an extended bridge, the first working surface of the first block and a third working surface of the bridge where the second block is attached form a continuous flat surface and are in the common plane; and the second block being attached to the bridge with the second working surface being against the third working surface of the bridge.

13. The system of claim 12, further comprising an arm extended towards the detector, a beamstop being attached to the arm and positioned to block the beam.

14. The system of claim 12, wherein the first block and the extended bridge form a "U" shaped block with two arms extending from the first block, the "U" shaped block having a flat and polished surface extending from the working surface of the first block to the working surfaces of the two arms, where the second block is attached with the second working surface against the working surface of the bridge arms.

15. The system of claim 12, wherein the said second block is a blade attached to the bridge of the first block and the second working surface is an edge of the blade.

16. The system of claim 11, wherein the crystal material comprises a single crystal material.

17. The system of claim 11, wherein the crystal material is mosaic crystal material.

18. A Kratky assembly comprising:
a first block with a first working surface, the working surface being flat and polished;
a second block with a second working surface, the first and second blocks being aligned with the first working surface pointing an opposite direction of the second working surface and the first working surface being aligned in a common plane with the second working surface,
an extension of the first block extending towards the detector and being configured to position a beamstop, the beamstop being attached to the extension and positioned to block a direct beam.

19. The assembly of claim 18, wherein the first block has an extended bridge, the first working surface of the first block and a third working surface of the bridge where the second block is attached form a continuous flat surface and are in the common plane; and the second block being attached to the bridge with the second working surface being against the third working surface of the bridge.

20. The assembly of claim 19, wherein the first block and the extended bridge form a "H" shaped block with two arms extending from the first block toward the second block and two arms extending from the first block toward the beamstop, the "H" shaped block having a flat and polished surface extending from the working surface of the first block to the working surfaces of the two arms extending toward the second block, where the second block is attached with the second working surface against the working surface of the two arms extending toward the second block.

* * * * *